US00PP07802P

United States Patent [19]

van Andel

[11] Patent Number: Plant 7,802

[45] Date of Patent: Feb. 18, 1992

[54] CARNATION NAMED 'STADIA'

[75] Inventor: Jacob van Andel, Aalsmeer, Netherlands

[73] Assignee: Van Staavern, B.V., Aalsmeer, Netherlands

[21] Appl. No.: 541,523

[22] Filed: Jun. 21, 1990

[51] Int. Cl.[5] ..... A01H 5/00

[52] U.S. Cl. ..... Plt./70

[58] Field of Search ..... Plt./70, 72, 73

*Primary Examiner*—Howard J. Locker

[57] ABSTRACT

A new and original mini-spray carnation variety particularly distinguished by the unusual red purple coloration of its small sized blossoms, which are produced intermittently during the Spring, Summer, and Fall blooming periods; the plant itself having a vigorous and upright growth habit and a height of about 100 cm.

1 Drawing Sheet

BACKGROUND OF THE NEW PLANT

This new mini-spray carnation cultivar originated as a hybrid seedling developed by me in 1980 at our nursery in Aalsmeer, Holland by crossing two varieties selected from our collection of carnations maintained for breeding purposes at Aalsmeer. This particular seedling was selected for propagation because of its unusual solid red flower coloration and the overall high quality of the plant growth. Asexual propagation of this selected plant was done by means of cuttings under my direction at Aalsmeer. Propagation of this new plant by cuttings continued from generation to generation to determine whether the novel characteristics of the selected seedling would be retained from generation to generation and its homogeneity could be assured. This proved to be successful and this new mini-spray carnation variety is now being propagated at Aalsmeer.

DESCRIPTION OF THE DRAWING

My new mini-spray carnation cultivar is illustrated by the accompanying photographic drawing, which shows blooming portions of spray stems with buds and flowers in several stages of development, the color rendition being as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Seedling.

Parentage:

*Seed parent.*—D.Barbatus (unpatented).

*Pollen parent.*—Plant number 81130-2J (unpatented).

Classification:

*Botanic.*—Dianthus Hybrid.

*Commercial.*—Mini-spray Carnation.

Form: Strong, erect bush with hardly any shoots at the flower stem nodes.

Height: About 100 cm, in average.

Main stem:

*Length.*—In average, about 50 cm.

*Growth.*—Vigorous and upright.

*Branching character.*—Hardly any shoots in the flower stem nodes.

Foliage:

*Number of leaves.*—Varies with the daylight length of the seasons.

*Leaf size.*—About 150 mm long and 11 mm wide at the fifth node.

*Leaf shape.*—Long, elliptical, with entire margins.

*Texture.*—Leathery.

*Color.*—Both upper and under side are dark green.

THE BUD

Size: Small.

*Diameter.*—Averaging about 7 mm.

*Length.*—Averaging about 20 mm.

Shape: Cylindrical.

Calyx:

*Shape.*—Cylindrical.

*Size.*—Averaging 8 mm in width and 20 mm in length.

*Splitting.*—The calyx does not split.

*Aspect.*—Smooth.

Flower stem:

*Character.*—Erect and strong.

*Color.*—Green 137-B.

*Length.*—Averaging 90 to 110 cm.

THE FLOWER

Blooming habit: Intermittent.

Size of flower: Small.

*Diameter.*—Averaging about 30 mm.

*Depth.*—Averaging about 10 mm.

Borne: In a cluster.

Shape:

*When first opening.*—Flat.

*When mature.*—Flattened dome-like center.

Petalage:

*Number of petals.*—About 18 to 20.

*Texture.*—Soft.

*Appearance.*—Velvety.

*Color.*—Both outer petals and inside petals.

*Body.*—61B.

*Base.*—White.
*Fragrance.*—Strong.
*Reverse side.*—61C.

Discoloration after full bloom: Color becomes somewhat darker.

Persistence: The flowers hang on and dry.

Disease resistance: Resistant to *Fusarium oxysporum.*

Frost tolerance: Low.

Lasting quality: Averaging about 14 days as a cut flower and 21 days on the plant.

REPRODUCTIVE ORGANS

Stamens:
*Number.*—10 to 15.

*Arrangement.*—Petaloid.
*Anthers.*—Size: About 2 mm. Color: White.

Pistils:
*Number.*—1.
*Styles.*—2. Length: About 20 mm. Color: 61B.
*Stigmas.*—Color: 61-B.

I claim:

1. The new and distinctive carnation plant, substantially as herein shown and described, particularly characterized by the red purple coloration of its flowers and the intermittent and profuse production of flowers on strong, upright stem.

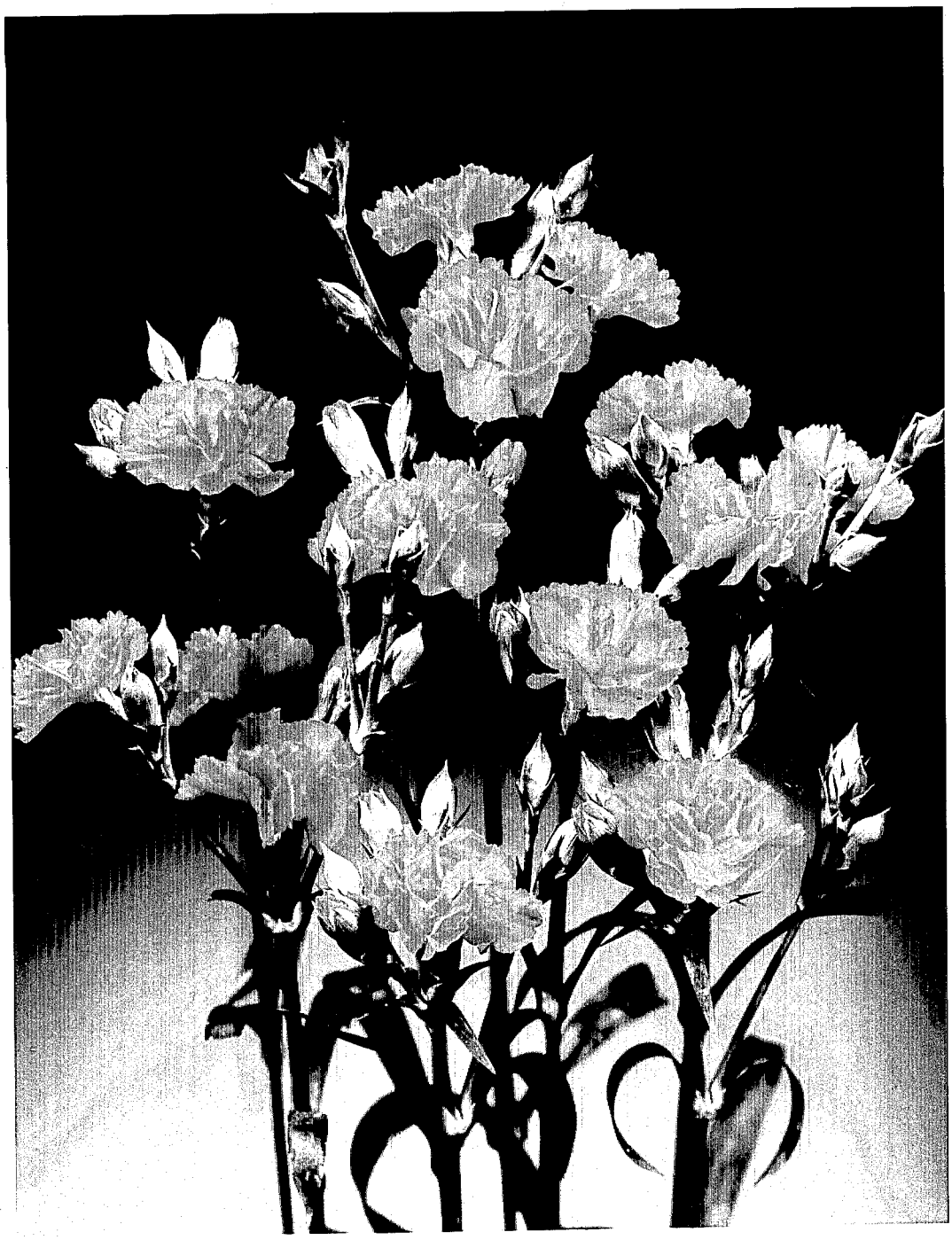

* * * * *